United States Patent [19]

Weaver et al.

[11] Patent Number: 4,994,512
[45] Date of Patent: Feb. 19, 1991

[54] POLY-METHINE COMPOUNDS, CONDENSATION POLYMER HAVING A POLY-METHINE COMPOUND ADMIXED THEREIN AND SHAPED ARTICLES PRODUCED THEREFROM

[75] Inventors: Max A. Weaver; Clarence A. Coates; Wayne P. Pruett, all of Kingsport; Samuel D. Hilbert, Jonesborough, all of Tenn.

[73] Assignee: Eastman Kodak Company, Rochester, N.Y.

[21] Appl. No.: 345,277

[22] Filed: May 1, 1989

[51] Int. Cl.$^5$ .................... C08K 5/41; C08K 5/16; C07C 121/72; C07C 125/06; C07C 147/06
[52] U.S. Cl. ........................... 524/209; 524/83; 524/84; 524/94; 524/100; 524/106; 524/170; 524/199; 524/208; 544/216; 548/141; 548/207; 548/317; 548/337; 549/63; 549/495; 558/401
[58] Field of Search ............... 558/401; 524/207, 208, 524/209, 170, 199, 84, 100, 106, 83, 94; 549/63, 495; 548/337, 141, 317, 207; 544/216

[56] References Cited

U.S. PATENT DOCUMENTS

| | | | |
|---|---|---|---|
| 3,546,270 | 12/1970 | Kirchmayr et al. | 524/209 |
| 3,706,700 | 12/1972 | Kirchmayr | 106/178 |
| 4,504,419 | 3/1985 | Dexter et al. | 558/401 |

FOREIGN PATENT DOCUMENTS 747688 5/1970 Belgium .
2123383 12/1971 Fed. Rep. of Germany .

OTHER PUBLICATIONS

B. Ranby & J. F. Rabek "Photodegradation, Photo-Oxidation and Photostabilization of Polymers" pp. 392–406 (1975).

Primary Examiner—Veronica P. Hoke
Attorney, Agent, or Firm—J. Frederick Thomsen; William P. Heath, Jr.

[57] ABSTRACT

Disclosed are poly-methine compounds having the formula:

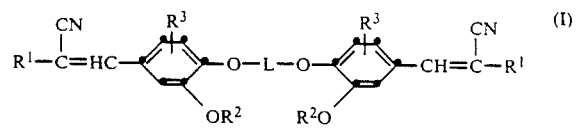

wherein
$R^1$ is an unsubstituted or substituted alkoxycarbonyl, cycloalkoxycarbonyl or aryloxycarbonyl radical; an unsubstituted or substituted carbamoyl radical; or an unsubstituted or substituted alkylsulfonyl, cycloalkylsulfonyl or arylsulfonyl radical, or an unsubstituted or substituted aryl radical;
$R^2$ is an unsubstituted or substituted alkyl, cycloalkyl or aryl radical;
$R^3$ is hydrogen, alkyl, —$OR^2$ or halogen; and
L is an organic linking group bonded by non-oxo carbon atoms to the oxygen atoms adjacent to L. Also disclosed are admixtures of about 100 to 10,000 ppm of at least one of the poly-methine compounds and certain condensation polymers. The resulting polymer compositions are useful to protect substrates or materials susceptible to degradation by ultraviolet light.

15 Claims, No Drawings

POLY-METHINE COMPOUNDS, CONDENSATION POLYMER HAVING A POLY-METHINE COMPOUND ADMIXED THEREIN AND SHAPED ARTICLES PRODUCED THEREFROM

This invention pertains to certain novel polymethine compounds and to novel condensation polymers, such as polyesters and polycarbonates, having one or more of the poly-methine compounds admixed therein. This invention also pertains to shaped articles such as film, sheet material and, especially, containers, such as those suitable for packaging beverages and foods, produced from the novel poly-methine compound-condensation polymer admixture.

Many products such as certain fruit juices, soft drinks, wines, food products, condiments, flavoring agents, cosmetics and shampoos are deleteriously affected, i.e., degraded, by ultraviolet (UV) light when packaged in clear plastic containers which pass significant portions of the available light at wavelengths in the range of approximately 250 to 390 nm. It is well known that polymers can be rendered resistant to degradation by UV light by physically blending in such polymers various UV light stabilizers such as benzophenones, benzotriazoles and resorcinol monobenzoates. See, for example, Plastics Additives Handbook, Hanser Publishers, Library of Congress, Catalog No. 83-062289, pp 128-134. Normally, such stabilizers are used in a weight concentration of at least 0.5 percent. Although these stabilizers generally function well to absorb radiation in the range of about 300 to 350 nm, absorbance in such range is not adequate to protect various substrates subject to UV light degradation packaged in or protected by clear plastic, i.e., colorless, transparent plastics.

Certain known stabilizers employed in stabilized polymer compositions can be extracted from the polymer by solvents such as acids, alcohols and the like present in foods or beverages packaged within the stabilized polymers. Many UV-absorbing compounds impart to polymers a yellow tint which is undesirable for many applications, e.g., in the manufacture of colorless, transparent poly(ethylene terephthalate) film, sheet material and containers. Furthermore, many compounds used to stabilize polymers are not stable at high temperatures and decompose under the conditions at which polyesters are manufactured or processed. Decomposition of such stabilizers frequently causes yellow discoloration of the polymer and results in the polymer containing little, if any, of the stabilizer. Yet another disadvantage inherent in many of the known UV absorbers is their tendency to sublime when exposed to the high temperatures employed by modern machines designed for the processing of thermoplastic, condensation polymer compositions. Such sublimation results in the loss of the UV absorber and contamination of the equipment.

U.S. Pat. No. 3,634,320 discloses bis-methine compounds having the general formula:

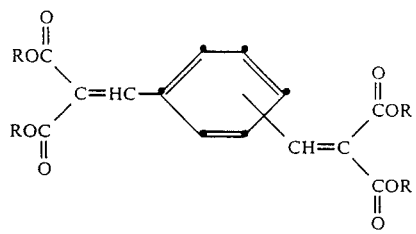

and their use as UV absorbers in polymeric compositions. The bis-methine compounds are employed in stabilizing amounts, e.g., in concentrations up to 5 weight percent, preferably 0.1 to 0.2 weight percent. These bis-methine compounds do not effectively absorb UV light in the 350 to 400 nm range.

U.S. Pat. No. 3,706,700 discloses the use of certain bis-methine compounds as light stabilizers and light filters in various polymeric materials. This patent discloses the compound having the structure:

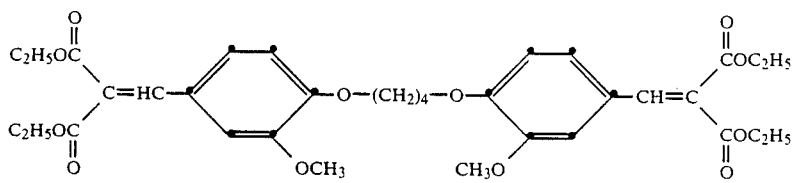

Compound (g) of Table Ia

This compound does not effectively absorb UV light having wavelengths greater than 350 nm.

The novel poly-methine compounds provided by our invention have the general formula:

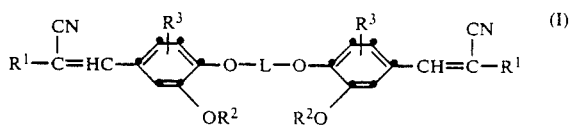

wherein

R$^1$ is an unsubstituted or substituted alkoxycarbonyl, cycloalkoxycarbonyl or aryloxycarbonyl radical; an unsubstituted or substituted carbamoyl radical; or an unsubstituted or substituted alkylsulfonyl, cycloalkylsulfonyl or arylsulfonyl radical, or an unsubstituted or substituted aryl radical;

R$^2$ is an unsubstituted or substituted alkyl, cycloalkyl or aryl radical;

R$^3$ is hydrogen, alkyl, —OR$^2$ or halogen; and

L is an organic linking group bonded by non-oxo carbon atoms to the oxygen atoms adjacent to L.

The alkyl and alkoxy moieties of the groups recited in the definitions of R$^1$ and R$^2$ can be unsubstituted or substituted alkyl and alkoxy of up to about 20 carbon atoms. Hydroxy, alkoxy, halogen, alkanoyloxy, alkoxycarbonyl, cyano, aryl, aryloxy, cycloalkyl, cycloalkoxy and alkylthio are examples of the substituents which may be present on the substituted alkyl groups and alkoxy moieties which R$^1$ and R$^2$ can represent. The cycloalkyl moieties of the groups recited in the definitions of R$^1$ and R$^2$ can be unsubstituted cycloalkyl of 5 to 7 carbon atoms which may be substituted with alkyl or any of the substituents mentioned hereinabove.

The carbamoyl groups which $R^1$ can represent may be unsubstituted or substituted carbamoyl such as N-alkylcarbamoyl, N,N-dialkylcarbamoyl, N-cycoalkylcarbamoyl, N-alkyl-N-cycloalkylcarbamoyl, N-arylcarbamoyl, N-alkyl-N-arylcarbamoyl and the like. The substituted carbamoyl groups include cyclic groups in which the carbamoyl nitrogen atom is a ring member, e.g., morpholinocarbonyl, piperidinocarbonyl and piperazinocarbonyl radicals. The aryl moieties of the groups recited in the definitions of $R^1$ and $R^2$ can be unsubstituted or substituted carbocyclic or heterocyclic aryl containing 6 to about 12 carbon atoms. Examples of the substituents which may be present on the aryl groups include alkyl and the substituents set forth in the preceding paragraph. Pyrrolyl, pyridyl, pyrimidyl, 2-benzothiazolyl, 2-benzoxazolyl, 2-benzimidazolyl, 2- or 3-thienyl, 2- or 3-furanyl, 1,3,4-thiadiazol-2-yl, 1,2,4-thiadiazol-2-yl, 1,2-benzisoxazol-3-yl, 1,2-benzisothiazol-3-yl, indolyl, 1,3,4-triazol-2-yl, quinolyl, 2-thiazolyl, and groups having the structure:

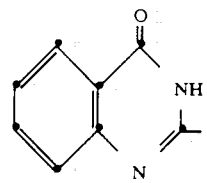

are examples of the unsubstituted aromatic heterocyclic residues which each $R^1$ or $R^2$ may represent.

The organic linking represented by L is bonded to the adjacent oxygen atoms through non-oxo carbon atoms, e.g., unsubstituted or substituted methylene groups, a methylidene group and an unsubstituted methylene group or a nuclear carbon atom of a carbocyclic or heterocyclic aromatic group. Thus, linking group L is selected from a wide variety of alkylene, alkenylene, alkynylene, cycloalkylene, carbocyclic and heterocyclic arylene and combinations of such divalent groups. The alkylene linking groups may contain within their main chain hetero atoms, e.g., oxygen, sulfur, sulfonyl, nitrogen, substituted nitrogen, and/or cyclic groups such as cycloalkylene, carbocyclic arylene, or divalent aromatic heterocyclic groups. Examples of alkylene linking groups containing additional hetero atoms within their chain include the following: alkylene-O-alkylene, alkylene-O-alkylene-O-alkylene, alkylene-S-alkylene,

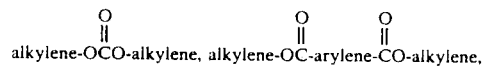

alkylene—$SO_2$—alkylene, etc.

Examples of alkylene linking groups containing a cyclic moiety in the linking chain include:

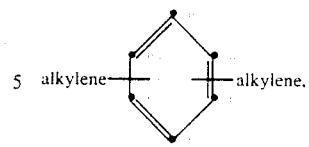

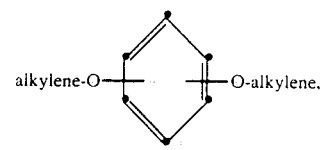

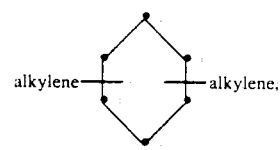

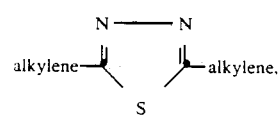

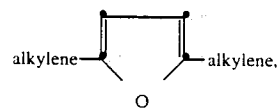

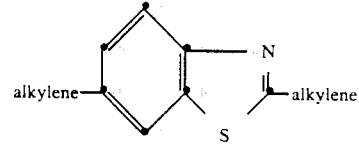

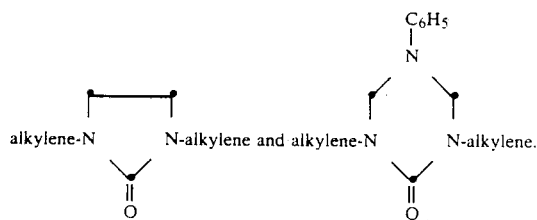

The carbocyclic groups may be cycloalkylene such as 1,2-, 1,3- and 1,4-cyclohexylene, 1,2-, 1,3- and 1,4-phenylene and 2,6- and 2,7-naphthylene. Examples of the divalent heterocyclic groups include unsubstituted and substituted triazines such as 1,3,5-triazin-2,4-diyl, 6-methoxy-1,3,5-triazin-2,4-diyl and the group having the structure:

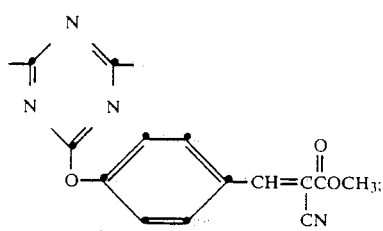

diazines such as 2,4-pyrimidindiyl, 6-methyl-2,4-pyrimidindiyl, 6-phenyl-2,4-pyrimidindiyl, 3,6-pyridazindiyl and 2-methyl-3-oxo-4,5-pyridazindiyl;

dicyanopyridines such as 3,5-dicyano-2,6-pyridindiyl and 4-phenyl-3,5-cyano-2,6-pyridindiyl; quinolines and isoquinolines such as 2,4-quinolindiyl and 2,8-isoquinolinediyl; quinoxalines such as 2,3-quinoxalindiyl; and azoles such as 2,5-thiazoldiyl, 5-methylene-2-thiazolyl, 3,5-isothiazoldiyl, 5-methylene-3-isothiazolyl, 1,3,4-thiadiazol-2,5-diyl, 1,2,4-thiadiazol-3,5-diyl, 2,6-benzothiazoldiyl, 2,5-benzoxazoldiyl, 2,6-benzimidazoldiyl, 6-methylene-2-benzothiazolyl and the group having the structure:

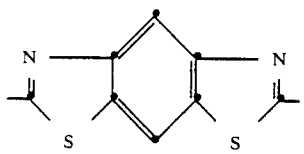

and maleimides such as 1-methyl-3,4-maleimidediyl and 1-phenyl-3,4-maleimidediyl. The acyclic moieties of the linking group represented by L also may be substituted, for example, with hydroxy, alkoxy, halogen, alkanoyloxy, cyano, alkoxycarbonyl, aryl, aryloxy, cycloalkyl, etc. The cyclic moieties of linking group L may be substituted with alkyl as well as with the substituents already mentioned. In addition to the possible substitution described above, the nitrogen atom of the nitrogen containing alkylene groups may be substituted, for example, with alkyl, aryl, alkanoyl, aroyl, alkylsulfonyl, or carbamoyl, e.g.,

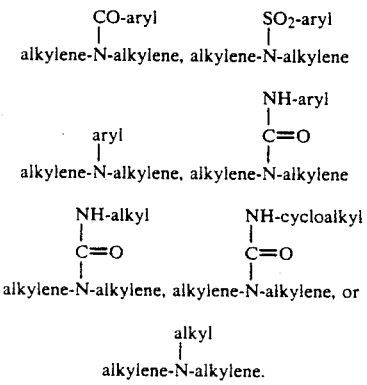

The preferred compounds of our invention are bis-methine compounds having the formula:

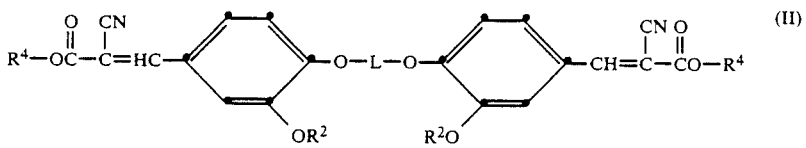

wherein
$R^2$ is alkyl of up to about 8 carbon atoms;
$R^4$ is alkyl of up to about 12 carbon atoms, cyclohexyl or phenyl; and
L is alkylene of 2 to 12 carbon atoms such as ethylene, propylene, 1,3-propanediyl, 1,6-hexanediyl, 1,8-octanediyl, 1,12-dodecanediyl, 2-hydroxy-1,3-propanediyl, 2,2-dimethyl-1,3-propanediyl, 2-methyl-1,3-propanediyl, oxy-bis-ethylene, i.e., $CH_2CH_2OCH_2CH_2$-, sulfonyl-bis-ethylene, thio-bis-ethylene, 1,4-phenylene-bis-methylene, 1,4-cyclohexylene-bis-methylene, 1,4-phenylene-bis-(oxyethylene), i.e., $-CH_2CH_2O-C_6H_4-OCH_2CH_2-$, methylsulfonylimino-bis-ethylene, phenylimino-bis-ethylene, acetylimino-bis-ethylene, phenylsulfonylimino-bis-ethylene, 1,2-, 1,3- or 1,4-phenylene, 1,4-cyclohexylene, 1,4-phenylene-bis-ethylene, oxy-bis-1,4-butanediyl or phenylcarbamoylimino-bis-ethylene, i.e., $CH_2CH_2N-(C_6H_5NHCO)-CH_2CH_2-$.

The bis-methine compounds of formula (II) which are especially preferred are those wherein $R^2$ and $R^4$ are lower alkyl, particularly methyl and ethyl, and L is alkylene of 2 to 8 carbon atoms, phenylenedimethylene and phenylenediethylene.

The poly-methine compounds of formula (I) can be prepared using known procedures by reacting intermediate aldehyde compounds (III) with an active methylene compound (IV) under Knoevenagel reaction conditions, e.g.,

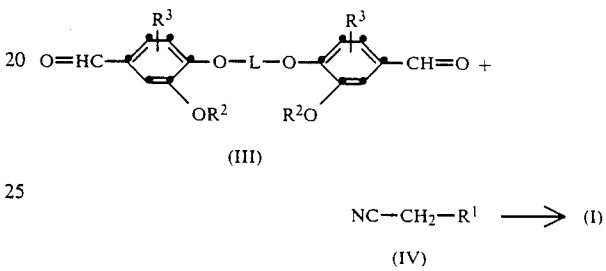

wherein $R^1$, $R^2$, $R^3$ and L are defined above.

The aldehyde compounds of formula (III) may be obtained by reacting dihalo compounds (V) with p-hydroxybenzaldehyde compounds (VI) according to methods known for the synthesis of ethers.

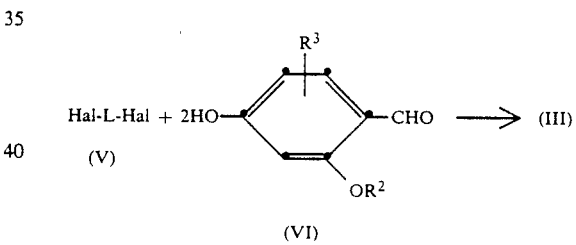

Suitable procedures are described in the chemical literature (W. J. P. Neish, Rec. trav. chim. 66, 433–42 (1947) [C.A. 42: 894a]; Hugh B. Donahue, et al., J. Org. Chem. 26, 474–6 (1961) [C.A. 55: 17565d]; R. Jaunin, et al., Helv. Chim. Acta. 42, 328–34 (1959). The poly-methine compounds in which L is a substituted alkylene group can be obtained by first reacting p-hydroxybenzaldehyde compounds (VI) with a dihaloalkanol such as 1,3-dichloro-2-propanol, 2,3-dibromopropanol or 1,4-dibromo-2-butanol to obtain compounds of formula (II) wherein L is a hydroxyalkylene group. The hydroxy group present on the organic linking group L can be reacted with a variety of compounds to produce various substituents, e.g., chlorides, ethers and various types of esters.

The polymeric compositions provided by this invention comprise a physical admixture of a polymer selected from extrusion, molding and fiber grade, thermoplastic, linear polyester and polycarbonate with about 100 to 10,000 ppm, based on the weight of the polymer, of at least one poly-methine compound of formula (I). Normally, relatively thin film and thin-walled containers require higher levels of the poly-methine compounds to protect a substrate from UV degradation. Thus, the effective concentration of the poly-methine compounds needed in the polymer decreases as the thickness of the film or container formed from the polymer increases.

The polyesters which may be used in the preparation of the compositions of our invention include linear, thermoplastic, crystalline or amorphous polyesters produced by conventional polymerization techniques from one or more diols and one or more dicarboxylic acids. The polyesters normally have an inherent viscosity (IV) of about 0.4 to about 1.2. The preferred polyesters comprise at least about 50 mole percent terephthalic acid residues and at least about 50 mole percent ethylene glycol and/or 1,4-cyclohexanedimethanol residues. Particularly preferred polyesters are those containing from about 75 to 100 mole percent terephthalic acid residues and from about 75 to 100 mole percent ethylene glycol residues.

The diol components of the described polyesters may be selected from ethylene glycol, 1,4-cyclohexanedimethanol, 1,2-propanediol, 1,3-propanediol, 1,4-butanediol, 2,2-dimethyl-1,3-propanediol, 1,6-hexanediol, 1,2-cyclohexanediol, 1,4-cyclohexanediol, 1,2-cyclohexanedimethanol, 1,3-cyclohexanedimethanol, X,8-bis(hydroxymethyl)-tricyclo-[5.2.1.0]-decane wherein X represents 3, 4, or 5; and diols containing one or more oxygen atoms in the chain, e.g., diethylene glycol, triethylene glycol, dipropylene glycol, tripropylene glycol and the like. In general, these diols contain 2 to 18, preferably 2 to 8 carbon atoms. Cycloaliphatic diols can be employed in their cis or trans configuration or as mixtures of both forms.

The acid components (aliphatic, alicyclic, or aromatic dicarboxylic acids) of the linear polyester are selected, for example, from terephthalic acid, isophthalic acid, 1,4-cyclohexanedicarboxylic acid, 1,3-cyclohexanedicarboxylic acid, succinic acid, glutaric acid, adipic acid, sebacic acid, 1,12-dodecanedioic acid, 2,6-naphthalene-dicarboxylic acid and the like. In the polymer preparation, it is often preferable to use a functional acid derivative thereof such as the dimethyl, diethyl, or dipropyl ester of the dicarboxylic acid. The anhydrides or acid halides of these acids also may be employed where practical.

Typical polycarbonates useful herein are disclosed in Kirk-Othmer Encyclopedia of Chemical Technology, third edition, Volume 18, pages 479–494, incorporated herein by reference.

The novel polymer compositions provided by this invention are useful in the manufacture of containers or packages for comestibles such as beverages and foods. By the use of known heat-setting techniques, certain of the polyesters are, in terms of color, I.V. and heat distortion, stable at temperatures up to about 100° C. Such stability characteristics are referred to herein as "hot-fill" stability. Articles molded from these polyesters exhibit good thin-wall rigidity, excellent clarity and good barrier properties with respect to moisture and atmospheric gases, particularly carbon dioxide and oxygen.

The linear polyesters most preferred for use in our invention comprises poly(ethylene terephthalate) and poly(ethylene terephthalate) wherein up to 5 mole percent of the ethylene glycol residues have been replaced with residues derived from 1,4-cyclohexanedimethanol and wherein the polyesters have been sufficiently heat set and oriented by methods well known in the art to give a desired degree of crystallinity. By definition, a polymer is "hot-fill" stable at a prescribed temperature when less than 2% change in volume of a container manufactured therefrom occurs upon filling the same with a liquid at the temperature. For the manufacture of blow-molded beverage bottles, the most preferred polyesters have an I.V. of 0.65 to 0.85, and a glass transition temperature (Tg) of >70° C., and film sections cut from the bottle have a Water Vapor Transmission Rate of 1.5 to 2.5 g mils/100 in.$^2$—24 hours, a Carbon Dioxide Permeability of 20–30 cc. mils/100 in.$^2$—24 hours -atm., and an Oxygen Permeability of 4–8 cc. mils/100 in.$^2$—24 hours -atm. The Tg is determined by Differential Scanning Calorimetry at a scan rate of 20 Centigrade Degrees/min., the Oxygen Permeability by the standard operating procedure of a MOCON OXTRAN 100 instrument of Modern Controls, Inc., of Elk River, Minn., and the Carbon Dioxide Permeability by the standard operating procedure of a MOCON PERMATRAN C II, also of Modern Controls.

The concentration of the poly-methine compound in the condensation polymer can be varied substantially depending, for example, on the intended function of the UV-absorbing residue and/or the end use for which the polymer composition is intended. When the polymer composition is to be used in the fabrication of relatively thin-walled containers, e.g., about 10 to 30 mils thick, to screen UV light in the range of about 250 to 390 nm, the concentration of the poly-methine compound normally will be in the range of about 50 to 1500 ppm (parts by weight per million parts by weight polymer) with the range of about 200 to 800 ppm being especially preferred. For polymer compositions destined for extrusion into thin film, e.g., 1 to 10 mils thick, concentrations of about 1000 to 10,000 ppm of the poly-methine compound normally will be used. For example, for equivalent protection from UV light, a 7 mil-thick film will contain about 1600 ppm whereas a 2 mil-thick film will contain about 6000 ppm of one of the poly-methine compounds.

The preparation of the novel poly-methine compound and their use in preparing the compositions of our invention are further illustrated by the following examples.

EXAMPLE 1

To a solution of vanillin (4-hydroxy-3-methoxybenzaldehyde, 91.2 g, 0.60 mol) dissolved in water (500 mL) containing sodium hydroxide (24.0 g, 0.60 mol) is added 1,2-dibromoethane (56.7 g, 0.30 mol) and the reaction mixture is stirred and heated at reflux for 8 hours and then allowed to cool. The product, 4,4'-[(1,2-ethanediyl)bis(oxy)bis(3-methoxybenzaldehyde)], is collected by filtration, washed with water and dried in air. A yield of 67.5 g (68% of theoretical yield) of a slightly gray solid is obtained. The identity of the product is supported by mass spectroscopy analysis.

A mixture of 4,4'-[(1,2-ethanediyl)bis(oxy)bis(3-methoxybenzaldehyde)] (49.5 g, 0.15 mol), methyl cyanoacetate (30 g, 0.30 mol), N,N-dimethylformamide (500 mL), piperidine (3 mL) and acetic acid (1 mL) is heated with stirring at about 100° C. for 2 hours. The reaction mixture is allowed to cool to room temperature and the pale yellow solid which forms is collected by filtration and washed with methanol. The crude product is reslurried in 500 mL of boiling methanol, collected by filtration, washed with methanol and dried in air. A yield of 59.4 g (81% of theory) of dimethyl 3,3'-[(1,2-ethanediyl)bis(oxy)bis(3-methoxy-4,1-phenylene)-bis(2-cyano-2-propenoate)] having the formula:

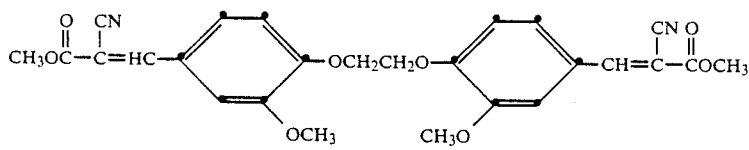

is obtained. The bis-methine compound has an absorption maximum (λmax) at 365 nm in methylene chloride in the UV absorption spectrum (ε=46,856).

EXAMPLE 2

To a solution of vanillin (91.2 g, 0.60 mol) dissolved in water (500 mL) containing sodium hydroxide (24.0 g, 0.60 mol) is added 1,3-dichloro-2-propanol (38.7 g, 0.30 mol) and the reaction mixture is stirred and heated at reflux for 8 hours and then allowed to cool. The product, 4,4'-[(2-hydroxy-propanediyl)bis(oxy)bis(3-methoxybenzaldehyde)], is collected by filtration, washed with water and dried in air. The product is recrystallized from 2 L of ethanol and collected by filtration, washed with ethanol and dried in air. A yield of 67.5 g (68% of theoretical yield) of an almost white solid is obtained. The identity of the product is supported by mass spectroscopy analysis.

A mixture of 4,4'-[(2-hydroxy-1,3-propanediyl)bis-(oxy)bis(3-methoxybenzaldehyde)] (3.60 g, 0.01 mol), ethyl cyanoacetate (2.26 g, 0.02 mol), ethanol (100 mL), piperidine (10 drops) and acetic acid (5 drops) is heated at reflux for 4 hours and then allowed to cool to room temperature. The essentially white product, diethyl 3,3'-[(2-hydroxy-1,3-propanediyl)bis(oxy)bis(3-methoxy-4,1-phenylene)bis(2-cyano-2-propenoate)], is collected by filtration, washed with ethanol and dried in air. Mass spectroscopy analysis confirms the product to have the formula:

This bis-methine compound has an absorption maximum at 360 nm in methylene chloride.

EXAMPLE 3

To a solution of vanillin (30.4 g, 0.30 mol) dissolved in water (150 mL) containing sodium hydroxide (8.5 g) is added 1,4-dibromo-2-butene (21.4 g, 0.10 mol) and the reaction mixture is stirred and heated at reflux for 6 hours and then allowed to cool. The product is collected by filtration, washed with water and dried in air and then recrystallized from 200 mL of toluene and again collected by filtration and dried in air. The yield of 4,4'-[(2-butene-1,4-diyl)bis(oxy)bis(3-methoxybenzaldehyde)] obtained is 18.8 g (52.8% of theory). The identity of the product is supported by mass spectroscopy analysis.

A mixture of 4,4'-[(2-butene-1,4-diyl)bis(oxy)bis(3-methoxybenzaldehyde)] (3.56 g, 0.01 mol), ethyl cyanoacetate (2.26 g, 0.02 mol), ethanol (90 mL) and piperidine (10 drops) is heated at reflux for 4 hours and then allowed to cool to room temperature. The product, diethyl 3,3'-[(2-butene-1,4-diyl)bis(oxy)bis(3-methoxy-4,1-phenylene)bis(2-cyano-2-propenoate)], (4.3 g) is collected by filtration, washed with ethanol and dried in air. Mass spectroscopy analysis confirms the product to have the formula:

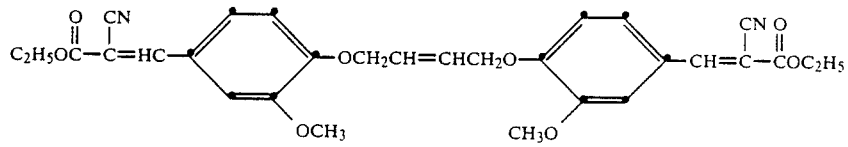

This bis-methine compound has an absorption maximum at 361 nm in methylene chloride.

EXAMPLE 4

A mixture of 4,4'-[(2-hydroxy-1,3-propanediyl)bis-(oxy)bis(3-methoxybenzaldehyde)] (3.60 g, 0.01 mol) and methylsulfonylacetonitrile (2.38 g, 0.02 mol) are reacted in ethanol according to the procedure described in Example 2 to obtain 4.0 g of 3,3'-[(2-hydroxy-1,3-propanediyl)bis(oxy)bis(3-methoxy-4,1-phenylene)-bis(2-methylsulfonyl)-2-propenenitrile]. Mass spectroscopy analysis confirms the product to have the formula:

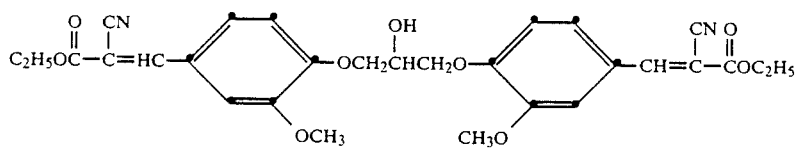

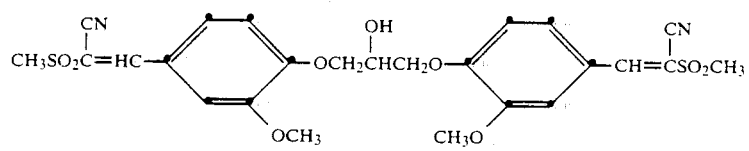
This bis-methine compound has an absorption maximum at 361 nm in methylene chloride.
Additional examples of our novel poly-methine compounds are set forth in Table I. These compounds conform to formula (II) and may be prepared according to the procedures described hereinabove.

TABLE I

| Example | R¹ | R² | R³ | L |
|---|---|---|---|---|
| 5 | —COOCH₃ | —CH₃ | H | —(CH₂)₄— |
| 6 | —COOC₂H₅ | —CH₃ | H | —CH₂CH₂OCH₂CH₂— |
| 7 | —COOCH₂CH₂OH | —CH₃ | H | —CH₂CH₂SCH₂CH₂— |
| 8 | —COOCH₂CH₂OC₂H₅ | —CH₃ | H | —CH₂CH₂SO₂CH₂CH₂— |
| 9 | —COOCH₂CH₂Cl | —CH₃ | H | —CH₂C₆H₄-4-CH₂— |
| 10 | —COOCH₂CH₂CN | —CH₃ | H | —CH₂C₆H₁₀-4-CH₂— |
| 11 | —COOCH₂C₆H₅ | —CH₃ | H | —CH₂CH₂OC₆H₄-4-OCH₂CH₂— |
| 12 | —COOCH₂CH₂OC₆H₅ | —CH₃ | H | —CH₂CH₂OC(O)OCH₂CH₂— |
| 13 | —COOCH₂C₆H₁₁ | —CH₃ | H | —CH₂CH₂OC(O)C₆H₄-4-C(O)OCH₂CH₂— |
| 14 | —COOC₆H₁₀-4-CH₃OH | —CH₃ | H | —CH₂CH₂OC(O)(CH₂)₄C(O)OCH₂CH₂— |
| 15 | —COOCH₂CH₂SCH₂CH₂OH | —CH₃ | H | 1,4-C₆H₄— |
| 16 | —COOCH₂CH₂NHCOCH₃ | —CH₃ | H | 1,3-C₆H₄— |
| 17 | —COOCH₂CH₂NCOCH₂CH₂CO | —CH₃ | H | —(CH₂)₃— |
| 18 | —COOCH₂CH(OH)CH₂OH | —CH₃ | H | —CH₂CH(OH)CH₂— |
| 19 | —COOCH₂CH(Cl)CH₂Cl | —CH₃ | H | —CH₂CCH₂OH |
| 20 | —COOCH₂CH(CH₂)₃O | —CH₃ | H | —CH₂CH(OOCCH₃)CH₂— |
| 21 | —COOC₆H₁₁ | —CH₃ | H | —CH₂CH(Cl)CH₂— |
| 22 | —COOCH(CH₃)₂ | —CH₃ | H | —CH₂CH(OCH₃)CH₂— |
| 23 | —COOC₅H₉ | —CH₃ | H | —CH₂CH(CN)CH₂— |
| 24 | —COOCH₃ | —CH₃ | H | —CH₂CH[OC₆H₄-4-CH=C(CN)COOCH₃]CH₂— |
| 25 | —COO(CH₂)₄H | —CH₃ | H | —CH₂CH₂OOCNHC₆H₃(4-CH₃)-3-NHCOOCH₂CH₂— |
| 26 | —COO(CH₂)₆OH | —CH₃ | H | —CH₂CH(OC₆H₅)CH₂— |
| 27 | —COO(CH₂)₄OOCCH₃ | —CH₃ | H | —CH₂CH(SC₆H₅)CH₂— |
| 28 | —COOC₂H₅ | —C₂H₅ | H | —CH₂CH(SO₂C₆H₅)CH₂— |
| 29 | —COOCH₂CH(C₂H₅)(CH₂)₄H | —(CH₂)₄H | H | —CH₂CH₂— |
| 30 | | —CH₂CH₂OH | H | —(CH₂)₄— |
| 31 | —COOCH₂C=CHCH=CHO | | H | —CH₂CH₂N(CH₃)CH₂CH₂— |
| 32 | —COOCH₂CH₂OOCCH₃ | —CH₂C₆H₅ | H | —CH₂CH₂N(SO₂CH₃)CH₂CH₂— |
| 33 | —COOCH₂CH₂OOC₂H₅ | —CH₂CH₂OC₆H₅ | H | —CH₂CH₂N(SO₂C₆H₅)CH₂CH₂— |
| 34 | —COOCH₂CH(OOCCH₃)CH₂Cl | —CH₂C₆H₁₁ | H | —CH₂CH₂N(COC₆H₅)CH₂CH₂— |
| 35 | —COO(CH₂CH₂O)₂H | —C₆H₅ | H | —CH₂CH₂N(CONHC₆H₅)CH₂CH₂— |
| 36 | —COO(CH₂CH₂O)₂COCH₃ | —C₆H₁₁ | 3-CH₃ | —CH₂CH₂N(CONHC₆H₁₁)CH₂CH₂— |
| 37 | —COOCH₂CH(OH)CH₂OH | —CH₃ | 2-Cl | —CH₂CH₂N(COCH₃)CH₂CH₂— |
| 38 | —COOCH₂CH(OOCCH₃)CH₂OOCCH₃ | —CH₃ | 3,5-di-CH₃ | —CH₂CH(OOCCH₃)CH₂— |
| 39 | —COOCH₂CH₂SCH₂CH₂OOCCH₃ | —CH₃ | 2-OCH₃ | —CH₂CH(OOCC₆H₅)—CH₂— |
| 40 | —COO(CH₂)₄COOC₂H₅ | —CH₃ | H | —CH₂CH(OOCNHC₆H₅)CH₂— |
| 41 | —COOCH₃ | —CH₃ | H | —CH₂CH=CHCH₂— |
| 42 | —COOC₂H₅ | —CH₃ | H | —CH₂C≡CCH₂— |
| 43 | —COOC₂H₅ | —CH₃ | H | —CH₂C(CH₃)₂CH₂— |

TABLE I-continued

| Example | R¹ | R² | R³ | L |
|---|---|---|---|---|
| 44 | —COOCH₂CH₂NCOC₆H₄-2-CO | —CH₃ | H | —CH₂CH₂OCH₂CH₂— |
| 45 | —COOCH₂CH₂OC₂H₅ | —CH₃ | H | —CH₂CH₂OOCC₆H₄-3-COOCH₂CH₂— |
| 46 | —COOCH₂CH₂OC₆H₄-4-COOCH₃ | —CH₃ | H | —CH₂CH₂OOCNH(CH₂)₄NHCOOCH₂CH₂— |
| 47 | —COOCH₂CH₂S(CH₂)₄H | —CH₃ | H | —CH₂NCH₂CH₂N(CH₂—)CO |
| 48 | —COOCH₂CH₂SC₆H₅ | —CH₃ | H | —CH₂CH₂OOCCH₂CH₂— |
| 49 | —COO(CH₂)₃CONH₂ | —CH₃ | H | —CH₂C₁₀H₆-4-CH₂— |
| 50 | —COOC₂H₅ | —CH₃ |  | —C=NC(OC₂H₅)=NC=N— |
| 51 | —SO₂CH₃ | —CH₃ | H | —CH₂CH₂— |
| 52 | —SO₂C₂H₅ | —CH₃ | H | —(CH₂)₄— |
| 53 | —SO₂(CH₂)₄H | —CH₃ | H | —CH₂C₆H₄-4-CH₂— |
| 54 | —SO₂CH₂C₆H₅ | —CH₃ | H | —CH₂C₆H₁₀-4-CH₂— |
| 55 | —SO₂CH₂C₆H₁₁ | —CH₃ | H | -1,4-C₆H₁₀— |
| 56 | —SO₂C₆H₅ | —CH₃ | H | —CH₂CH₂OC₆H₄-4-OCH₂CH₂— |
| 57 | —SO₂C₆H₄-4-CH₃ | —CH₃ | H | —CH₂C₆H₁₀-4-CH₂— |
| 58 | —SO₂C₆H₃-3,4-di-Cl | —CH₃ | H | —CH₂C(CH₃)₂CH₂— |
| 59 | —SO₂C₆H₄-2-Br | —CH₃ | H | —CH₂CH₂SCH₂CH₂— |
| 60 | —SO₂C₆H₃-3,4-di-OCH₃ | —CH₃ | H | —CH₂CH₂SO₂CH₂CH₂— |
| 61 | —SO₂C₆H₄-4-OC₂H₅ | —CH₃ | H | —CH₂CH₂N(SO₂CH₃)CH₂CH₂— |
| 62 | —SO₂C₆H₄-3-CH₃ | —CH₃ | H | —CH₂CH₂N(COCH₃)CH₂CH₂— |
| 63 | —SO₂CH₃ | —CH₃ | H | —CH₂CH=CHCH₂— |
| 64 | —SO₂CH₃ | —C₂H₅ | H | —CH₂C≡CCH₂— |
| 65 | —SO₂C₂H₅ | —CH₂C₆H₅ | H | —CH₂CH(OH)CH₂— |
| 66 | —SO₂CH₂CH(CH₃)₂ | —C₆H₁₁ | H | —CH₂CH(OOCCH₃)CH₂— |
| 67 | —SO₂CH₂CH₂OC₆H₅ | —C₆H₅ | H | —CH₂CH₂OOC(CH₂)₄COOCH₂CH₂— |
| 68 | —SO₂C₆H₁₁ | —C₆H₅ |  | —C=NC(OC₂H₅)=NC=N— |
| 69 | —SO₂C₆H₄-4-NHCOCH₃ | —CH₃ | 2-OC₂H₅ | —CH₂CH₂OC₆H₄-4-OCH₂CH₂— |
| 70 | —SO₂C₆H₄-4-NHSO₂CH₃ | —CH₃ | 2-Br | -1,4-C₆H₄— |
| 71 | —SO₂C₆H₄-3-CF₃ | —CH₃ | 3,5-di-CH₃ | —CH₂CH₂OCOCH₂CH₂— |
| 72 | —SO₂CH₂C=CHCH=CHO | —CH₃ | H | —CH₂CH₂OOCC₆H₄-3-COOCH₂CH₂— |
| 73 | —SO₂C₆H₃-2,5-di-CH₃ | —CH₃ | H | —CH₂CH₂OOCNHC₆H₄-4-CH₃-3-NHCOOCH₂CH₂— |
| 74 | —SO₂C₆H₃-2-OCH₃-5-Cl | —CH₃ | H | —CH₂CH(Cl)CH₂— |
| 75 | —SO₂CH₂CH₂OCH₂CH₃ | —CH₃ | H | —CH₂CH(OOCCH₃)CH₂— |
| 76 | —SO₂CH₂SC₆H₅ | —CH₃ | H | —CH₂CH(CN)CH₂— |
| 77 | —SO₂CH₂C₆H₁₁ | —CH₃ | H | —CH₂C₁₀H₆-4-CH₂— |

TABLE I-continued

| Example | R¹ | R² | R³ | L |
|---|---|---|---|---|
| 78 | —CONH₂ | —CH₃ | H | —(CH₂)₄— |
| 79 | —CONHCH₃ | —CH₃ | H | —CH₂CH₂— |
| 80 | —CONH(CH₂)₄H | —CH₃ | H | —(CH₂)₄— |
| 81 | —CONHCH₂CH₂OH | —CH₃ | H | —(CH₂)₃— |
| 82 | —CONH(CH₂)₃OC₂H₅ | —CH₃ | H | —CH₂CH₂OCH₂CH₂— |
| 83 | —CONHCH₂C₆H₅ | —CH₃ | H | —CH₂CH₂SCH₂CH₂— |
| 84 | —CONHCH₂C₆H₁₁ | —CH₃ | H | —CH₂CH₂SO₂CH₂CH₂— |
| 85 | —CONHC₆H₁₁ | —CH₃ | H | —CH=CHCH₂— |
| 86 | —CONHC₆H₅ | —CH₃ | H | —(CH₂)₄— |
| 87 | —CONHC₆H₄-2-OCH₃ | —CH₃ | H | —CH₂CH₂OC₆H₁₀-4-OCH₂CH₂— |
| 88 | —CONHC₆H₄-4-CH₃ | —CH₃ | H | —CH₂C₆H₁₀-4-CH₂— |
| 89 | —CONHC₆H₄-3-Cl | —CH₃ | H | —CH₂C₆H₁₀-4-CH₂— |
| 90 | | —CH₃ | H | —CH₂CH₂OCOOCH₂CH₂— |
| 91 | —CONHC=N-o-C₆H₄S | —CH₃ | H | —CH₂CH₂OOC(CH₂)₄COOCH₂CH₂— |
| 92 | —CONHC=NNC(CH₃)S | —CH₃ | H | —CH₂CH₂OOCC₆H₄-3-COOCH₂CH₂— |
| 93 | —CONHC=CHCH=CHN=CH | —CH₃ | H | —CH₂CH(OH)CH₂— |
| 94 | —CON(CH₃)₂ | —CH₃ | H | —CH₂CH(OOCCH₃)CH₂— |
| 95 | —CON(CH₃)C₂H₅ | —CH₃ | H | —CH₂CH(Cl)CH₂— |
| 96 | —CON(CH₃)C₆H₅ | —(CH₂)₄H | H | —CH₂CH(OCH₃)CH₂— |
| 97 | —CON[(CH₂)₄H]C₆H₄-3-CH₃ | —CH₂C₆H₁₁ | H | —CH₂CH₂N(SO₂CH₃)CH₂CH₂— |
| 98 | —CON(CH₂CH₂OH)₂ | —CH₃ | 2-O(CH₂)₄H | —CH₂CH(CH₃)₂CH₂— |
| 99 | —CONHC₆H₃-2-OCH₃-5—S—CH₃ | —CH₃ | 2-Cl | —CH₂CH(OOCCH₃)CH₂— |
| 100 | —CONHC₆H₄-4-CH₂CH₂OH | —CH₃ | H | —CH₂CH₂— |
| 101 | —CONCH₂CH₂OCH₂CH₂ —CON(CH₂)₄ CH₂ | —CH₃ | H | —CH₂C≡CCH₂— |
| 102 | —CON(CH₂)₃ CH₂ | —CH₃ | H | -1,4-C₆H₄ |
| 103 | —CONCH₂CH₂N(COCH₃)CH₂ CH₂ | —CH₃ | H | -1,4-C₆H₁₀ |
| 104 | —CONCH₂CH₂SO₂CH₂ CH₂ | —CH₃ | H | —(CH₂CH₂O)₂CH₂CH₂— |
| 105 | —CONHCH₂C₆H₁₀-4-CH₂OH | —CH₃ | H | —CH₂C₁₀H₆-4-CH₂— |

TABLE I-continued

| Example | R¹ | R² | R³ | L |
|---|---|---|---|---|
| 106 | —C=N-o-$C_6H_4$—O— | —$CH_3$ | H | —$(CH_2)_4$— |
| 107 | —C=N-o-$C_6H_4$—NH— | —$CH_3$ | H | —$(CH_2)_4$— |
| 108 | —C=N-o-$C_6H_4$—S— | —$C_2H_5$ | H | —$(CH_2)_2$— |
| 109 | —C=N-o-$C_6H_4$—C(O)NH— | —$CH_3$ | H | —$CH_2CH_2OCH_2CH_2$— |
| 110 | —C=N-o-$C_6H_4$— | —$CH_3$ | H | —$(CH_2)_6$— |
| 111 | —C=N-S-o-$C_6H_4$— | —$(CH_2)_4H$ | H | —$(CH_2)_8$— |
| 112 | —C=N—N—C($CH_3$)—S— | —CH($CH_3$)_2 | H | —$CH_2CH_2OOC(CH_2)_4COOCH_2CH_2$— |
| 113 | —C=CHCH=C(Br)—S— | —$CH_2C_6H_5$ | H | —$CH_2CH(OH)CH_2$— |
| 114 | —C=CHNH-o-$C_6H_4$— | —$CH_2CH_2Cl$ | H | —$CH_2CH_2$— |
| 115 | —C=CHCH=CH—O— | —$CH_2CH_2OC_2H_5$ | H | —$CH_2CH_2$— |
| 116 | —C=CH-o-$C_6H_4$—N=CH— | —$CH_2CH_2OC_6H_5$ | H | —$CH_2CH_2$— |
| 117 | —$C_6H_3$-3,4-di-CN | —$CH_2C_6H_{11}$ | H | —$CH_2CH_2$— |
| 118 | —$C_6H_4$-4-COO$CH_3$ | —$CH_2CH_2OC_6H_{11}$ | H | —$CH_2CH_2$— |
| 119 | —$C_6H_4$-4-$SO_2CH_3$ | —$CH_2CH_2CN$ | H | —$CH_2CH_2$— |
| 120 | —C=NCH=CH—S— | —$CH_2CH_2NHCOCH_3$ | H | —$CH_2CH_2$— |

EXAMPLE 121

Four hundred grams of polyethylene terephthalate (I.V.=0.71) are dry blended with 0.32 g (800 ppm) of the bis-methine compound of Example 1. The blend is dried overnight (16 hours) in a vacuum oven at 110° C. After drying, the material is melt blended and extruded into 10 mil film on a C. W. Brabender ¾ inch extruder (25 to 1 L/D). A transmission spectrum of the 10 mil film obtained using a Perkin-Elmer Lambda 6 UV/Vis Spectrophotometer shows less than 6% transmission of light at any wavelength from 300 to 395 nm whereas a similarly produced 10 mil film using the commercial UV Absorber Tinuvin P at a concentration of 10,000 ppm blocks the transmission of light to only 385 nm. This example shows that significantly less of the UV absorbers of this IR are needed to block the transmission of harmful wavelengths of light than normal commercial materials.

The inherent viscosities (I.V.) of the polyesters described herein are determined at 25° C. using 0.5 g polymer per 100 mL of a solvent consisting of 60 parts by weight phenol and 40 parts by weight tetrachloroethane.

The invention has been described in detail with particular reference to preferred embodiments thereof, but it will be understood that variations and modifications can be effected within the spirit and scope of the invention.

We claim:

1. A polymeric composition comprising a physical admixture of a polymer selected from extrusion, molding and fiber grade, thermoplastic, linear polyester and polycarbonate with about 100 to 10,000 ppm, based on the weight of the polymer, of at least one poly-methine compound having the formula:

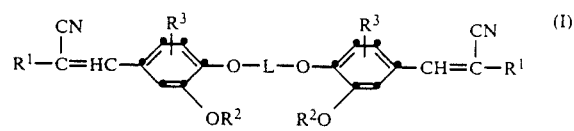

wherein
R$^1$ is an unsubstituted or substituted alkoxycarbonyl, cycloalkoxycarbonyl or aryloxycarbonyl radical; an unsubstituted or substituted carbamoyl radical; or an unsubstituted or substituted alkylsulfonyl, cycloalkylsulfonyl or arylsulfonyl radical or an unsubstituted or substituted aryl radical;
R$^2$ is an unsubstituted or substituted alkyl, cycloalkyl or aryl radical;
R$^3$ is hydrogen, alkyl, —OR$^2$ or halogen; and
L is an organic linking group bonded by non-oxo carbon atoms to the oxygen atoms adjacent to L.

2. A polymeric composition according to claim 1 wherein the polymer is a polyester having an inherent viscosity of about 0.4 to 1.2 comprised of at least 50 mole percent terephthalic acid residues and at least 50 mole percent of ethylene glycol, 1,4-cyclohexanedimethanol or a mixture thereof.

3. A polymeric composition comprising a physical admixture of an extrusion or molding grade, thermoplastic, linear polyester having an inherent viscosity of about 0.4 to 1.2 and comprising from about 75 to 100 mole percent terephthalic acid residues and from about 75 to 100 mole percent ethylene glycol residues with about 100 to 10,000 ppm, based on the weight of the polyester, of at least one poly-methine compound having the formula:

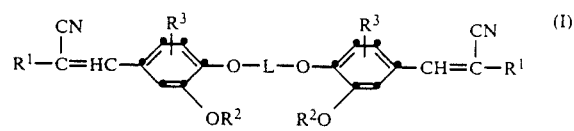

wherein
R$^1$ is an unsubstituted or substituted alkoxycarbonyl, cycloalkoxycarbonyl or aryloxycarbonyl radical; an unsubstituted or substituted carbamoyl radical; or an unsubstituted or substituted alkylsulfonyl, cycloalkylsulfonyl or arylsulfonyl radical;
R$^2$ is an unsubstituted or substituted alkyl, cycloalkyl or aryl radical;
R$^3$ is hydrogen, alkyl, —OR$^2$ or halogen; and
L is an organic linking group bonded by non-oxo carbon atoms to the oxygen atoms adjacent to L.

4. A polymeric composition according to claim 3 wherein the poly-methine compound has the formula:

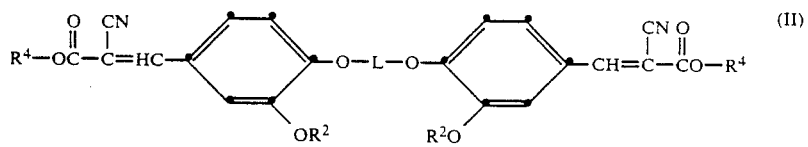

wherein
R$^2$ is alkyl of up to about 8 carbon atoms;
R$^4$ is alkyl of up to about 12 carbon atoms, cyclohexyl or phenyl; and
L is alkylene of 2 to 12 carbon atoms, 2-hydroxy-1,3-propanediyl, 2,2-dimethyl-1,3-propanediyl, 2-methyl-1,3-propanediyl, oxy-bis-ethylene, sulfonyl-bis-ethylene, thio-bis-ethylene, phenylenedimethylene, phenylenediethylene, 1,4-cyclohexylene-bis-methylene, 1,4-phenylene-bis-(oxyethylene), methylsulfonylimino-bis-ethylene, phenylimino-bis-ethylene, acetylimino-bis-ethylene, phenylsulfonylimino-bis-ethylene, 1,2-, 1,3- or 1,4-phenylene, 1,4-cyclohexylene or 1,4-phenylene-bis-ethylene.

5. A polymeric composition according to claim 4 wherein
R$^2$ is lower alkyl;
R$^4$ is lower alkyl; and
L is alkylene of 2 to 12 carbon atoms, phenylenedimethylene or phenylenediethylene.

6. A shaped article fabricated of the polymeric composition defined in claim 1.

7. The shaped article of claim 6 wherein the article is a film, sheet material or container.

8. A shaped article fabricated of a polymeric composition comprising a physical admixture of an extrusion or molding grade, thermoplastic, linear polyester having an inherent viscosity of about 0.4 to 1.2 and comprising from about 75 to 100 mole percent terephthalic acid residues and from about 75 to 100 mole percent ethylene glycol residues with about 100 to 10,000 ppm, based on the weight of the polyester, of at least one poly-methine compound having the formula:

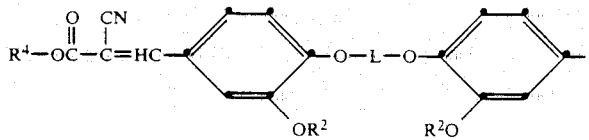

wherein
R² is alkyl of up to about 8 carbon atoms;
R⁴ is alkyl of up to about 12 carbon atoms, cyclohexyl or phenyl; and
L is alkylene of 2 to 12 carbon atoms, 2-hydroxy-1,3-propanediyl, 2,2-dimethyl-1,3-propanediyl, 2-methyl-1,3-propanediyl, oxy-bis-ethylene, sulfonyl-bis-ethylene, thio-bis-ethylene, phenylenedimethylene, phenylenediethylene, 1,4-cyclohexylene-bis-methylene, 1,4-phenylene-bis-(oxyethylene), methylsulfonylimino-bis-ethylene, phenylimino-bis-ethylene, acetylimino-bis-ethylene, phenylsulfonylimino-bis-ethylene, 1,2-, 1,3- or 1,4-phenylene, 1,4-cyclohexylene or 1,4-phenylene-bis-ethylene.

9. An article according to claim 8 wherein the article is a container comprising walls about 10 to 30 mils thick and the physical admixture contains about 50 to 1500 ppm of the poly-methine compound.

10. An article according to claim 9 wherein the physical admixture contains about 200 to 800 ppm of the poly-methine compound.

11. An article according to claim 8 wherein the article is a film about 1 to 10 mils thick and the physical admixture contains about 1000 to 10,000 ppm of the poly-methine compound.

12. An article according to claim 8 wherein the article is a film about 2 to 7 mils thick and the physical admixture contains about 1600 to 6000 ppm of the poly-methine compound.

13. A poly-methine compound having the formula:

$$\text{(I)}$$

wherein
R¹ is an unsubstituted or substituted alkoxycarbonyl, cycloalkoxycarbonyl or aryloxycarbonyl radical; an unsubstituted or substituted carbamoyl radical; or an unsubstituted or substituted alkylsulfonyl, cycloalkylsulfonyl or arylsulfonyl radical;
R² is an unsubstituted or substituted alkyl, cycloalkyl or aryl radical;
R³ is hydrogen, alkyl, —OR² or halogen; and
L is an organic linking group bonded by non-oxo carbon atoms to the oxygen atoms adjacent to L.

14. A poly-methine compound according to claim 13 wherein the poly-methine compound has the formula:

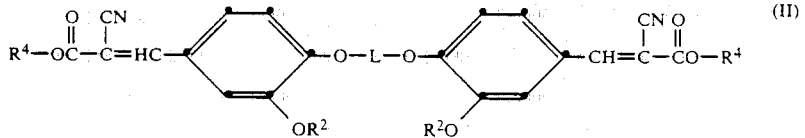

wherein
R² is alkyl of up to about 8 carbon atoms;
R⁴ is alkyl of up to about 12 carbon atoms, cyclohexyl or phenyl; and
L is alkylene of 2 to 12 carbon atoms, 2-hydroxy-1,3-propanediyl, 2,2-dimethyl-1,3-propanediyl, 2-methyl-1,3-propanediyl, oxy-bis-ethylene, sulfonyl-bis-ethylene, thio-bis-ethylene, phenylenedimethylene, phenylenediethylene, 1,4-cyclohexylene-bis-methylene, 1,4-phenylene-bis-(oxyethylene), methylsulfonylimino-bis-ethylene, phenylimino-bis-ethylene, acetylimino-bis-ethylene, phenylsulfonylimino-bis-ethylene, 1,2-, 1,3- or 1,4-phenylene, 1,4-cyclohexylene or 1,4-phenylene-bis-ethylene.

15. A poly-methine compound according to claim 14 wherein
R² is lower alkyl;
R⁴ is lower alkyl; and
L is alkylene of 2 to 8 carbon atoms, phenylenedimethylene or phenylenediethylene.

* * * * *